(12) United States Patent
Lee et al.

(10) Patent No.: US 10,093,752 B2
(45) Date of Patent: Oct. 9, 2018

(54) HOMOPOLYMER NANOPARTICLES BY SELF-EMULSION POLYMERIZATION REACTION AND PREPARATION METHOD THEREOF

(71) Applicant: GWANGJU INSTITUTE OF SCIENCE AND TECHNOLOGY, Gwangju (KR)

(72) Inventors: Jae-Suk Lee, Gwangju (KR); Santosh Kumar, Gwangju (KR); Dong Woo Kim, Gwangju (KR); Mohammad Changei, Gwangju (KR); Hong-Joon Lee, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 14/304,265

(22) Filed: Jun. 13, 2014

(65) Prior Publication Data

US 2014/0370114 A1 Dec. 18, 2014

Related U.S. Application Data

(60) Provisional application No. 61/834,436, filed on Jun. 13, 2013.

(30) Foreign Application Priority Data

Jan. 6, 2014 (KR) .................... 10-2014-0001067

(51) Int. Cl.
*C08F 2/00* (2006.01)
*C08F 120/00* (2006.01)
*C08F 126/00* (2006.01)
*A61K 9/51* (2006.01)
*C08F 2/22* (2006.01)
*C08F 120/20* (2006.01)
*C08F 120/42* (2006.01)
*C08F 120/06* (2006.01)
*C08F 126/06* (2006.01)
*C08F 126/10* (2006.01)

(52) U.S. Cl.
CPC .............. *C08F 2/22* (2013.01); *A61K 9/5138* (2013.01); *C08F 120/06* (2013.01); *C08F 120/20* (2013.01); *C08F 120/42* (2013.01); *C08F 126/06* (2013.01); *C08F 126/10* (2013.01)

(58) Field of Classification Search
CPC ........ C08F 2/22; C08F 120/06; C08F 120/20; C08F 120/42; C08F 126/06; C08F 126/10; A61K 47/50; A61K 9/5138; C08J 3/12
See application file for complete search history.

(56) References Cited

U.S. PATENT DOCUMENTS

| | | | | |
|---|---|---|---|---|
| 5,863,996 | A * | 1/1999 | Graham ................ | C08F 2/06 526/216 |
| 6,858,299 | B2 * | 2/2005 | Lundquist ............ | C08F 220/18 428/402 |
| 2003/0008989 | A1 * | 1/2003 | Gore .................... | C08F 2/06 526/227 |
| 2004/0236050 | A1 * | 11/2004 | Lundquist ............ | C08F 220/18 526/319 |
| 2005/0282011 | A1 * | 12/2005 | Yokoyama ........... | B01J 13/14 428/402.2 |

FOREIGN PATENT DOCUMENTS

EP 1088833 A1 * 4/2001 .............. C08F 2/22

OTHER PUBLICATIONS

Camli et al., J Colloid Interface Sci. Apr. 15, 2010;344(2):528-532.
J Colloid Interface Sci. Apr. 15, 2010;344(2):528-532.*
Egen et al. Surfactant-Free Emulsion Polymerization of Various Methacrylates: Towards Monodisperse Colloids for Polymer Opals. Macromol. chem. Phys. 2004, 205:1479-1488.*
Chern. Emulsion polymerization mechanisms and kinetics. Prog. Polym. Sci. 31 (2006) 443-486.*
Egen et al. Macromol. Surfactant-Free Emulsion Polymerization of Various Methacrylates: Towards Monodisperse Colloids for Polymer Opals. Chem. Phys. 2004, 205:1479-1488.*
Santosh Kumar et al., Exploration of the Mechanism for Self-Emulsion Polymerization of Amphiphilic Vinylpyridine, Published in the American chemical Society, Macromolecules, 46(18) , p. 7166-7172, Aug. 20, 2013.

* cited by examiner

*Primary Examiner* — Robert A Wax
*Assistant Examiner* — Olga V Tcherkasskaya
(74) *Attorney, Agent, or Firm* — Hauptman Ham, LLP

(57) ABSTRACT

Disclosed herein is a preparation method of homopolymer nanoparticles without using a surfactant. The homopolymer nanoparticles prepared thereby are expected to be widely used not only as a template of a semiconductor metal oxide, a drug delivery system (DDS), an electron transport layer (ETL), and a seed having vertical structural shape, but also in a high precision field such as replacement of an organic device polystyrene bead film.

8 Claims, 11 Drawing Sheets

HOMOPOLYMER NANOPARTICLES BY SELF-EMULSION POLYMERIZATION REACTION AND PREPARATION METHOD THEREOF

CROSS-REFERENCE TO RELATED APPLICATIONS

This application claims priority to Provisional Application Ser. No. 61/834,436 filed on 13 Jun. 2013, and Korean Patent Application No. 10-2014-0001067 filed on 6 Jan. 2014, and all the benefits accruing there from under 35 U.S.C. § 119, the contents of which is incorporated by reference in its entirety.

TECHNICAL FIELD

The present invention relates to homopolymer nanoparticles by a self-emulsion polymerization reaction and a preparation method thereof, and more particularly, to a preparation method of homopolymer nanoparticles by a self-emulsion polymerization reaction characterized by not using a surfactant.

The present invention also relates to a drug delivery material including the homopolymer nanoparticles and a preparation method thereof, and an electron transport layer including the homopolymer nanoparticles.

BACKGROUND

Polymer particles having good monodispersibility and a nano-sized diameter are drawing much attention and being studied hard, due to various industrial applications in nano-materials field demanding to be 'smaller', 'smarter' and 'faster'. According to the application fields of the nanoparticles, such particles may be used in very industrially important, high value-added materials, such as organic pigments for paints, color balls, a toner, a filler for chromatography, a diagnosis reagent, a chemical/biological sensor, microelectronics, a photonic crystal, a drug delivery material, and the like.

One of the preparation methods of such monodisperse polymer fine particles is emulsion polymerization. Emulsion polymerization which is a method of using a water-soluble, hydrophilic polymerization initiator in a water-insoluble monomer emulsified in water with an emulsifier, is easy to remove polymerization heat, has low viscosity of the emulsion, and has a high molecular weight of the polymer, since the reaction occurs in water. However, the emulsion is easily contaminated with the emulsifier, and it is costly to remove it.

As a prior art to overcome this problem, a polymerization method without an emulsifier, which is called, soap-free emulsion polymerization, is suggested. Soap-free emulsion polymerization which is a method of using a monomer and an ionic hydrophilic initiator or an ionic comonomer without adding an emulsifier, that is, a surfactant, has particularly good monodispersibility of the emulsion. As the mechanism of the method, there is a theory that a polymer adsorbs to a particle nucleus. According to the mechanism, a particle growth process depends on a deposition rate of polymer materials in a bulk; and if a hydrophilic initiator has high concentration, polymer materials in the bulk are increased, and larger particles are synthesized. However, the method has limitations such as a low reaction rate, and using only hydrophobic monomers.

SUMMARY

Thus, in order to overcome the foregoing problems, an object of the present invention is to provide a preparation method of homopolymer nanoparticles by self-emulsion polymerization, capable of forming a micelle without using a surfactant, and homopolymer nanoparticles prepared thereby.

Another object of the present invention is to provide a drug delivery material including the homopolymer nanoparticles, and a preparation method thereof.

Another object of the present invention is to provide an electron transport layer including the homopolymer nanoparticles.

In one general aspect, a preparation method of homopolymer nanoparticles, includes the following steps:

(a) obtaining a surfactant-free dispersion containing an amphiphilic monomer, a hydrophilic initiator and water; and (b) carrying out a self-emulsion polymerization reaction in the surfactant-free dispersion.

The homopolymer may be represented by the following Formula:

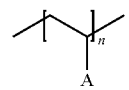

(wherein A is a substituted aryl group, a substituted or unsubstituted aromatic heterocyclic group, an alkyl halide group, a cyano group, a carboxyl group, an ester group, an amide group, a cyanate group, a thiocyanate group, a phosphate group, a sulfo group or a pyrrolidone group.)

The amphiphilic monomer may be represented by the following Formula:

(wherein A is a substituted aryl group, a substituted or unsubstituted aromatic heterocyclic group, an alkyl halide group, a cyano group, a carboxyl group, an ester group, an amide group or a pyrrolidone group.)

According to an exemplary embodiment of the present invention, the hydrophilic initiator may be at least one selected from the group consisting of 2,2'-azobis[2-(2-imidazolin-2-yl)propane]dihydrochloride, 4,4-azobis(4-cyanovaleric acid), ammonium persulfate, potassium persulfate, sodium persulfate, ammonium bisulfate, sodium bisulfate and 1,1-azobis(1-methylbutyronitrile-3-sodium sulfonate).

In another general aspect, homopolymer nanoparticles include a homopolymer represented by one of the following Chemical Formulae 1 to 8:

[Chemical Formula 1]

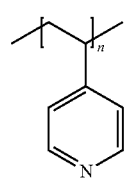

-continued

[Chemical Formula 2]
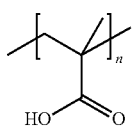

[Chemical Formula 3]
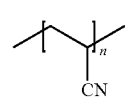

[Chemical Formula 4]
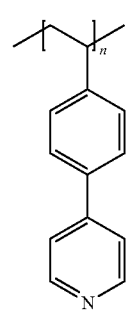

[Chemical Formula 5]
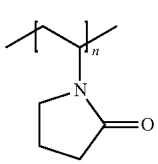

[Chemical Formula 6]
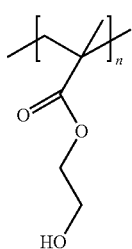

[Chemical Formula 7]
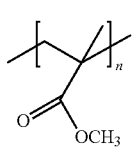

[Chemical Formula 8]
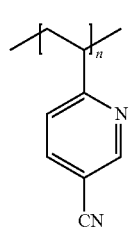

(wherein n is an integer of 10 to 10,000);

wherein the homopolymer nanoparticle has a spherical shape having a diameter of 1 to 800 nm;

consists of the 2 to 1,000 homopolymers; and has a shell composed of a hydrophilic pendant of the homopolymer consisting of a hydrophobic main chain and a hydrophilic pendant, and an inner layer composed of 70 to 95 vol % of a hydrophobic main chain and 5 to 30 vol % of a hydrophilic pendant of the homopolymer.

In another general aspect, a drug delivery material includes the homopolymer nanoparticles and a pharmaceutical active material collected in the inner layer of the homopolymer nanoparticles.

In another general aspect, a preparation method of a drug delivery material includes the following steps:

(a) obtaining a surfactant-free dispersion containing an amphiphilic monomer, a hydrophilic initiator, water and a pharmaceutical active material; and (b) carrying out a self-emulsion polymerization reaction in the surfactant-free dispersion;

wherein the drug delivery material contains the homopolymer nanoparticles and a pharmaceutical active material collected in the inner layer of the homopolymer nanoparticles;

the homopolymer nanoparticles include a homopolymer represented by one of the following Chemical Formulae 1 to 8:

[Chemical Formula 1]
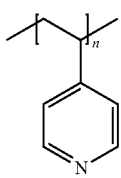

[Chemical Formula 2]
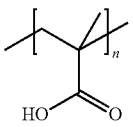

[Chemical Formula 3]

[Chemical Formula 4]
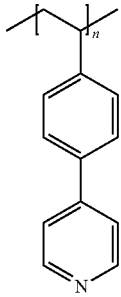

[Chemical Formula 5]
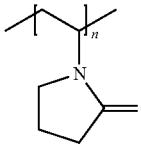

[Chemical Formula 6]
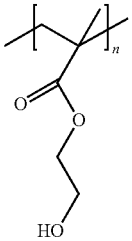

[Chemical Formula 7]
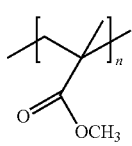

[Chemical Formula 8]
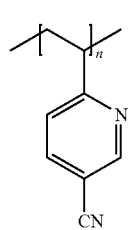

(wherein n is an integer of 10 to 10,000), the homopolymer nanoparticle having a spherical shape having a diameter of 1 to 800 nm, consisting of the 2 to 1,000 homopolymers, and having a shell composed of a hydrophilic pendant of the homopolymer consisting of a hydrophobic main chain and a hydrophilic pendant, and an inner layer composed of 70 to 95 vol % of a hydrophobic main chain and 5 to 30 vol % of a hydrophilic pendant of the homopolymer;

the amphiphilic monomer is at least one selected from the group consisting of vinylpyridine, 4-vinylpyridine, acrylic acid, methacrylic acid, styrene sulfonic acid, 4-styrene sulfonic acid, methylmethacrylate, 2-hydroxyethyl methacrylate, hydroxypropyl methacrylate, hydroxybutyl methacrylate, methacrylamide, N-vinylpyrrolidone, acrylonitrile, 4-(4-vinylphenyl)pyridine and 6-vinylpyridine-3-carbonitrile;

the hydrophilic initiator is at least one selected from the group consisting of 2,2'-azobis[2-(2-imidazolin-2-yl)propane]dihydrochloride, 4,4-azobis(4-cyanovaleric acid), ammonium persulfate, potassium persulfate, sodium persulfate, ammonium bisulfate, sodium bisulfate and 1,1-azobis(1-methylbutyronitrile-3-sodium sulfonate); and the self-emulsion polymerization reaction is carried out at 55 to 95° C. for 50 to 160 minutes.

In another general aspect, a preparation method of a drug delivery material includes the following steps:

(a) obtaining a surfactant-free dispersion containing an amphiphilic monomer, a hydrophilic initiator and water;

(b) carrying out a self-emulsion polymerization reaction in the surfactant-free dispersion, to prepare homopolymer nanoparticles; and (c) swelling the homopolymer nanoparticles and collecting a pharmaceutical active material in an inner layer of the homopolymer nanoparticles;

wherein the homopolymer nanoparticles consist of a homopolymer selected from the following Chemical Formulae 1 to 8:

[Chemical Formula 1]
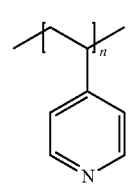

[Chemical Formula 2]
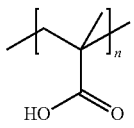

[Chemical Formula 3]
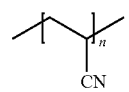

[Chemical Formula 4]
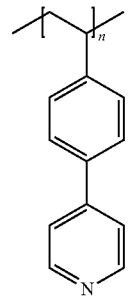

[Chemical Formula 5]
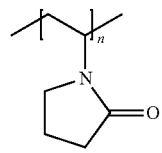

[Chemical Formula 6]
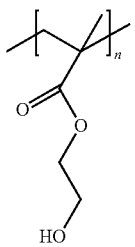

[Chemical Formula 7]
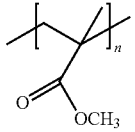

[Chemical Formula 8]
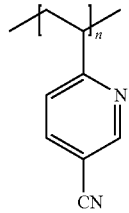

(wherein n is an integer of 10 to 10,000), the homopolymer nanoparticle having a spherical shape having a diameter of 1 to 800 nm, consisting of the 2 to 1,000 homopolymers, and having a shell composed of a hydrophilic pendant of the homopolymer consisting of a hydrophobic main chain and a hydrophilic pendant, and an inner layer composed of 70 to 95 vol % of a hydrophobic main chain and 5 to 30 vol % of a hydrophilic pendant of the homopolymer;

the amphiphilic monomer is at least one selected from the group consisting of vinylpyridine, 4-vinylpyridine, acrylic acid, methacrylic acid, styrene sulfonic acid, 4-styrene sulfonic acid, methylmethacrylate, 2-hydroxyethyl methacrylate, hydroxypropyl methacrylate, hydroxybutyl methacrylate, methacrylamide, N-vinylpyrrolidone, acrylonitrile, 4-(4-vinylphenyl)pyridine and 6-vinylpyridine-3-carbonitrile;

the hydrophilic initiator is at least one selected from the group consisting of 2,2'-azobis[2-(2-imidazolin-2-yl)propane]dihydrochloride, 4,4-azobis(4-cyanovaleric acid), ammonium persulfate, potassium persulfate, sodium persulfate, ammonium bisulfate, sodium bisulfate and 1,1-azobis (1-methylbutyronitrile-3-sodium sulfonate); and the self-emulsion polymerization reaction is carried out at 55 to 95° C. for 50 to 160 minutes.

In another general aspect, an electron transport layer includes the homopolymer nanoparticles as described above.

DETAILED DESCRIPTION

Hereinafter, the present invention will be described in detail.

Unless otherwise defined herein, "amphiphilic" means having both hydrophilic and hydrophobic properties in a molecule, "hydrophobic" means not easily combining with a water molecule, and "hydrophilic" means easily combining with a water molecule.

The present invention provides a preparation method of homopolymer nanoparticles using a self-emulsion polymerization reaction. A self-emulsion polymerization (SEP) uses a monomer having both a hydrophilic group and a hydrophobic group, thereby not using a surfactant, a crosslinker or an emulsifier. This leads to the elimination of an impurity removing step such as washing, purification and the like, and the homopolymer nanoparticles prepared thereby have no impurity therein.

The present invention provides a preparation method of a homopolymer nanoparticle, including the following steps:

(a) obtaining a surfactant-free dispersion containing an amphiphilic monomer, a hydrophilic initiator and water; and (b) carrying out a self-emulsion polymerization reaction in the surfactant-free dispersion.

Figure 1:
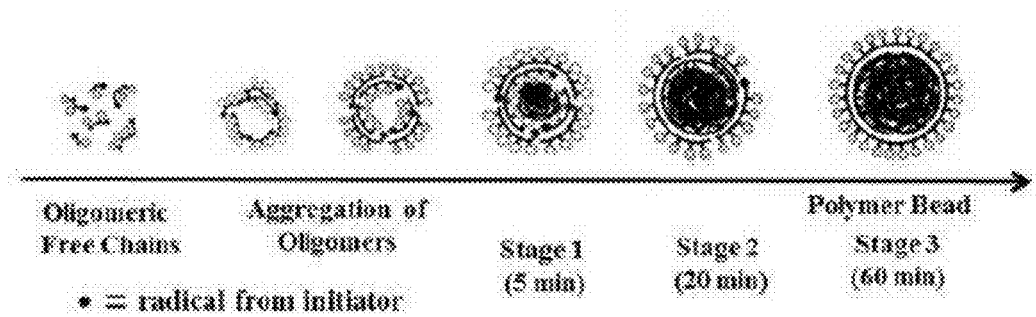
FIG. 1 shows a mechanism of a self-emulsion polymerization reaction process.
Figure 3:
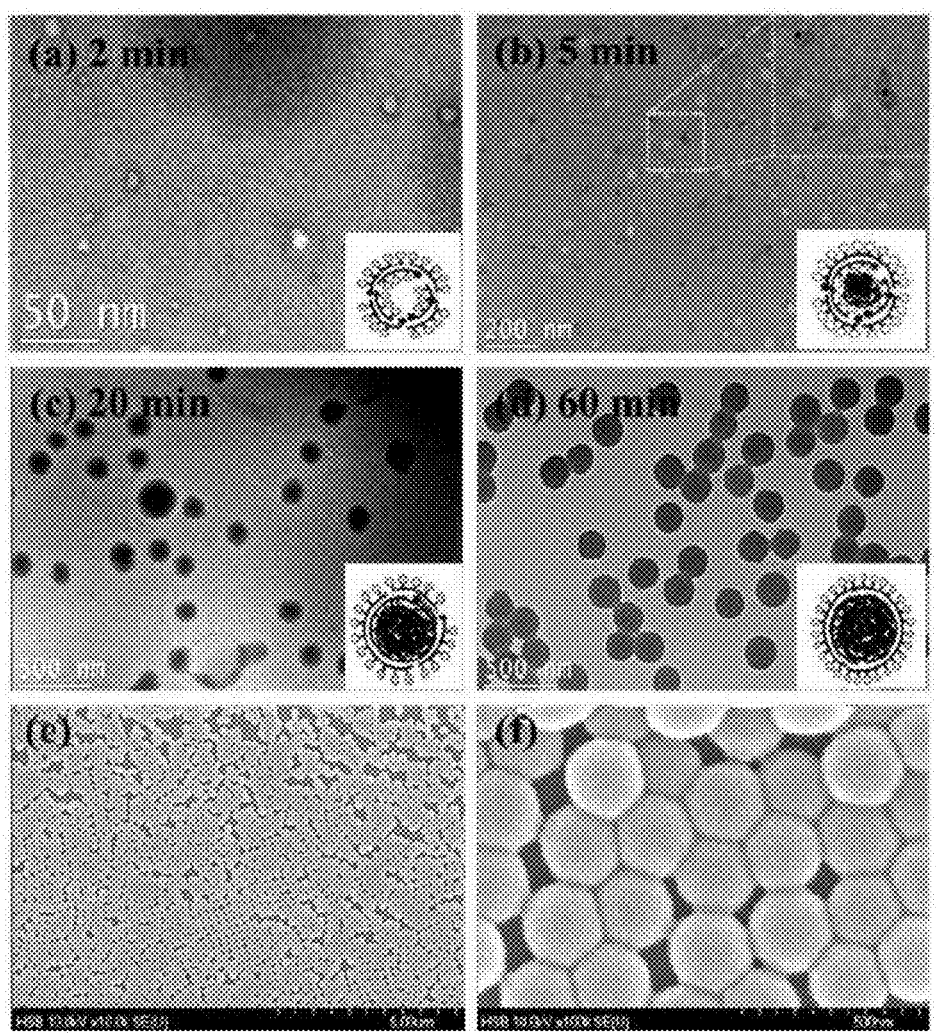
FIGS. 3(a) to 3(d) are transmission electron microscope (TEM) photographs of the nanoparticles prepared in Example 1.
FIGS. 3(e) and 3(f) are scanning electron microscope (SEM) photographs of the nanoparticles prepared in Example 1.

In order to prepare a homopolymer using the self-emulsion polymerization reaction, only water, a hydrophilic initiator and an amphiphilic monomer are used. FIG. 1 shows a mechanism of a self-emulsion polymerization reaction process. Addition of a hydrophilic initiator to water at constant temperature, allows addition polymerization of a hydrophilic initiator and an amphiphilic monomer, thereby forming a polymer. The hydrophilic portions of the polymer are together arranged, and the hydrophobic portions of the polymer are together arranged in water, respectively, thereby forming a micelle. Since the amphiphilic monomer or polymer serves as a surfactant, there is no need to use any surfactant as in an emulsion polymerization reaction. As the polymer is polymerized in the micelle, the micelles grow and form nanoparticles. FIGS. 3(a) to 3(d) are transmission electron microscope (TEM) photographs of poly-4-vinylpyridine homopolymer nanoparticles prepared by a self-emulsion polymerization reaction over time. As seen from FIG. 3(a), homopolymer chains start to make micelles with an empty inside. In FIG. 3(b), some dark parts represent polymer chains going into the inside of micelles. In FIGS. 3(c) and 3(d), micelles and polymers in the micelles grow to form nanoparticles, and after 60 minutes from reaction start, no more growth is identified.

Since the homopolymer nanoparticles prepared by the above method does not use a surfactant, thereby not containing impurities, they may be used in a drug delivery material or an electron transport layer, requiring high purity.

The homopolymer may be represented by the following Formula:

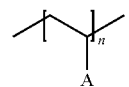

(wherein A is a substituted aryl group, a substituted or unsubstituted aromatic heterocyclic group, an alkyl halide group, a cyano group, a carboxyl group, an ester group, an amide group, a cyanate group, a thiocyanate group, a phosphate group, a sulfo group or a pyrrolidone group; and n is an integer of 10-10,000.)

In an exemplary embodiment of the present invention, the homopolymer may be one selected from the following Formulae 1 to 8:

[Chemical Formula 1]

[Chemical Formula 2]

[Chemical Formula 3]

[Chemical Formula 4]

[Chemical Formula 5]

[Chemical Formula 6]

[Chemical Formula 7]

[Chemical Formula 8]

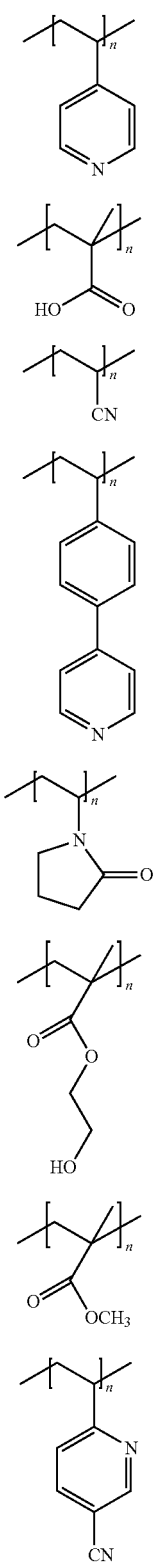

wherein n is an integer of 10 to 10,000.

In an exemplary embodiment of the present invention, the amphiphilic monomer has both hydrophilic and hydrophobic groups, and may be represented by the following Formula:

(wherein A is a substituted aryl group, a substituted or unsubstituted aromatic heterocyclic group, an alkyl halide group, a cyano group, a carboxyl group, an ester group, an amide group or a pyrrolidone group.)

The examples of the amphiphilic monomer may be at least one selected from the group consisting of vinylpyridine, 4-vinylpyridine, acrylic acid, methacrylic acid, styrene sulfonic acid, 4-styrene sulfonic acid, methylmethacrylate, 2-hydroxyethyl methacrylate, hydroxypropyl methacrylate, hydroxybutyl methacrylate, methacrylamide, N-vinylpyrrolidone, acrylonitrile, 4-(4-vinylphenyl)pyridine and 6-vinylpyridine-3-carbonitrile.

In another exemplary embodiment of the present invention, the hydrophilic initiator dissolves well in water and initiates a polymerization reaction of amphiphilic monomers; and the examples thereof may be at least one selected from the group consisting of 2,2'-azobis[2-(2-imidazolin-2-yl)propane]dihydrochloride, 4,4-azobis(4-cyanovaleric acid), ammonium persulfate, potassium persulfate, sodium persulfate, ammonium bisulfate, sodium bisulfate and 1,1-azobis(1-methylbutyronitrile-3-sodium sulfonate), but are not limited thereto. Specifically, the hydrophilic initiator may be 2,2'-azobis[2-(2-imidazolin-2-yl)propane]dihydrochloride.

In another exemplary embodiment of the present invention, the self-emulsion polymerization reaction may be carried out at 55-95° C. Below the lower limit, the reaction rate is so slow that the reaction time takes a long time, and above the upper limit, water which is the solvent evaporates to make the reaction difficult to occur.

In another exemplary embodiment of the present invention, the self-emulsion polymerization reaction may be carried out for 50-160 minutes. Below the lower limit, the polymerization reaction is not completed so that the nanoparticles continue to grow, and above the upper limit, the polymerization reaction is completed so that the particle size does not grow any more. As seen from FIG. 2, after 60 minutes from the initiation of the self-emulsion polymerization reaction, the particle size does not grow any more.

In addition, the present invention provides homopolymer nanoparticles prepared by the above method. The homopolymer nanoparticle has a spherical shape having a diameter of 1-800 nm; consists of the 2 to 1,000 homopolymers; and has a shell composed of a hydrophilic pendant of the homopolymer consisting of a hydrophobic main chain and a hydrophilic pendant, and an inner layer composed of 70 to 95 vol % of a hydrophobic main chain and 5 to 30 vol % of a hydrophilic pendant of the homopolymer.

Through the alteration of the condition of the self-emulsion polymerization reaction, the size of the homopolymer nanoparticles may be controlled. The size of the nanoparticles prepared by the self-emulsion polymerization reaction increases, as the concentrations of the hydrophilic initiator and the amphiphilic monomer are higher, and the size of the nanoparticles decreases, as the reaction temperature increases.

The more the hydrophilic initiators and the amphiphilic monomers are, the more the short-chained polymers which may serve as a surfactant are, which leads to the formation of more micelles. Also, as the number of the polymers capable of growing therein increases, the size of nanoparticles may be increased.

As seen from Table 3, in a self-emulsion polymerization reaction, as the temperature increases, the size of nanoparticles tends to decrease. This is because a propagation velocity of the amphiphilic monomers increases at high temperature, to reduce a rapid end and improve initiating efficiency. As a result, more ionic groups are involved in the stability of the nanoparticles, and the particle size is decreased.

In addition, the present invention provides a drug delivery material including the homopolymer nanoparticles and a pharmaceutical active material collected in the inner layer of the homopolymer nanoparticles.

In addition, the present invention provides the following steps, as a preparation method of the drug delivery material:

(a) obtaining a surfactant-free dispersion containing an amphiphilic monomer, a hydrophilic initiator, water and a pharmaceutical active material; and (b) carrying out a self-emulsion polymerization reaction in the surfactant-free dispersion. The drug delivery material includes the homopolymer nanoparticles of the present invention and a pharmaceutical active material collected in the inner layer of the homopolymer nanoparticles.

In addition, as another preparation method of the drug delivery material, a process of swelling the homopolymer nanoparticles prepared by the above method may be provided.

In addition, the present invention provides an electron transport layer including the homopolymer nanoparticles. In case of forming an electron transport layer using the homopolymer nanoparticles of the present invention, the morphology of the active layer on the electron transport layer is improved, and overall element performance may be improved.

Hereinafter, the present invention will be described in detail, by way of drawings, Examples, and Experiment Examples. However, those Examples, and Experiment Examples are intended to describe the present invention in more detail, and it will be evident to a person skilled in the art that the scope of the present invention is in no way limited thereby.

Example 1 Preparation of poly 4-vinylpyridine Homopolymer Nanoparticles 4-vinylpyridine (4-VP) and water were placed in a 500 mL flask, purged with argon for 30 minutes to remove oxygen, and stirred at 400 rpm at 65° C. for 5 minutes. A hydrophilic initiator (VA-044, chemical name: 2,2'-Azobis[2-(2-imidazolin-2-yl)propane]dihydrochloride) was added to the stirred solution. Stirring was carried out at 65° C. for 60 minutes to prepare poly 4-vinylpyridine homopolymer nanoparticles. The self-emulsion polymerization reaction of 4-VP homopolymer is represented by the following Reaction Formula 1.

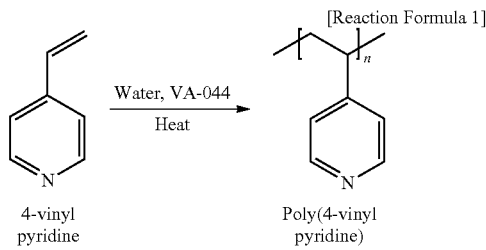

[Reaction Formula 1]

4-vinyl pyridine → Poly(4-vinyl pyridine)

Water, VA-044
Heat

The experiment results depending on the concentration of the hydrophilic initiator, the solvent concentration and the temperature are summarized in the following Tables 1 to 3.

TABLE 1

| Monomer 4VP (mmol) | Initiator VA-044 (mmol) | Solvent $H_2O$ (ml) | Time/Temperature (min/° C.) | Particle size (by DLS in nm) |
|---|---|---|---|---|
| 4.75 | 0.475 | 60 | 60/65 | 290 |
| 4.75 | 0.237 | 60 | 60/65 | 230 |
| 4.75 | 0.158 | 60 | 60/65 | 192 |
| 4.75 | 0.118 | 60 | 60/65 | 183 |
| 4.75 | 0.016 | 60 | 60/65 | 80 |

TABLE 2

| Monomer 4VP (mmol) | Initiator VA-044 (mmol) | Solvent $H_2O$ (ml) | Time/Temperature (min/° C.) | Particle size (by DLS in nm) |
|---|---|---|---|---|
| 4.75 | 0.475 | 30 | 60/65 | 316 |
| 4.75 | 0.475 | 60 | 60/65 | 200 |
| 4.75 | 0.475 | 90 | 60/65 | 180 |
| 4.75 | 0.475 | 120 | 60/65 | 140 |
| 4.75 | 0.475 | 150 | 60/65 | 90 |

TABLE 3

| Temperature (° C.) | Particle size (by DLS in nm) |
|---|---|
| 65 | 190 |
| 75 | 180 |
| 85 | 160 |

Figure 2:
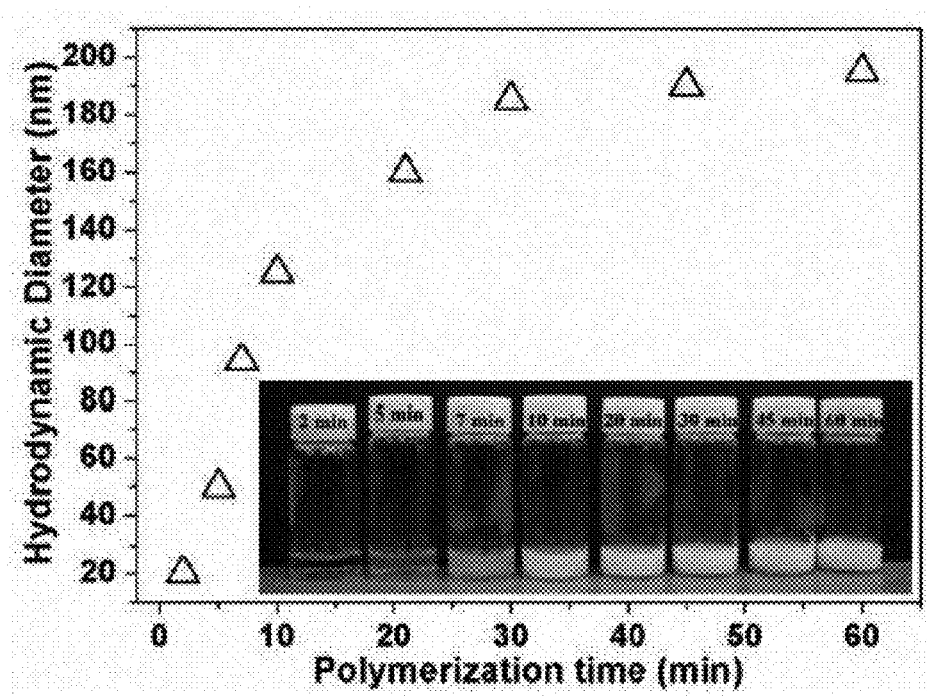
FIG. 2 is a graph with a photograph representing the size of poly 4-vinylpyridine homopolymer nanoparticles over the reaction time of a self-emulsion polymerization.
Figure 4:
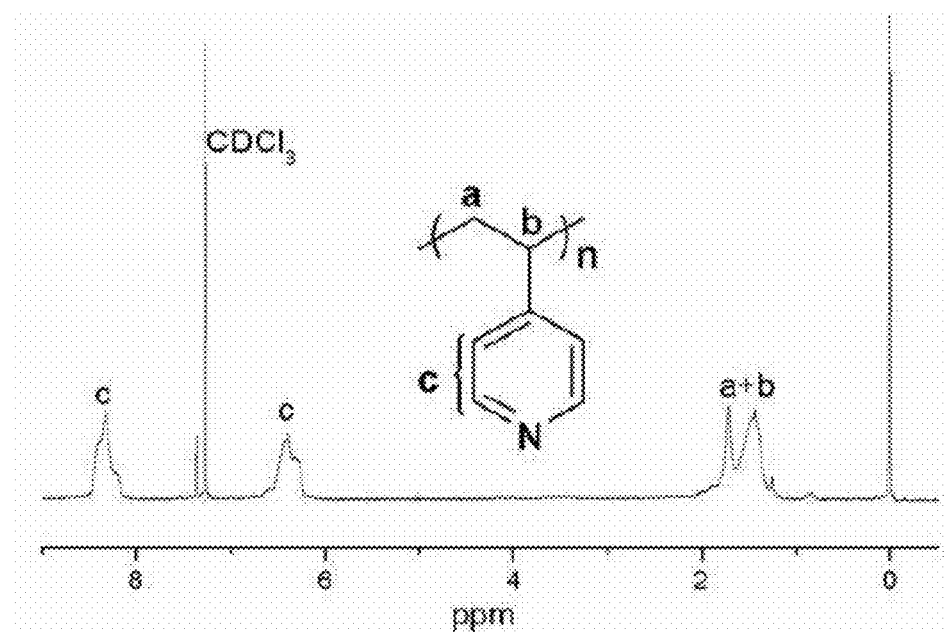
FIG. 4 is a graph representing a 1H-nuclear magnetic resonance (NMR) spectrum of the nanoparticles prepared in Example 1.
Figure 5:
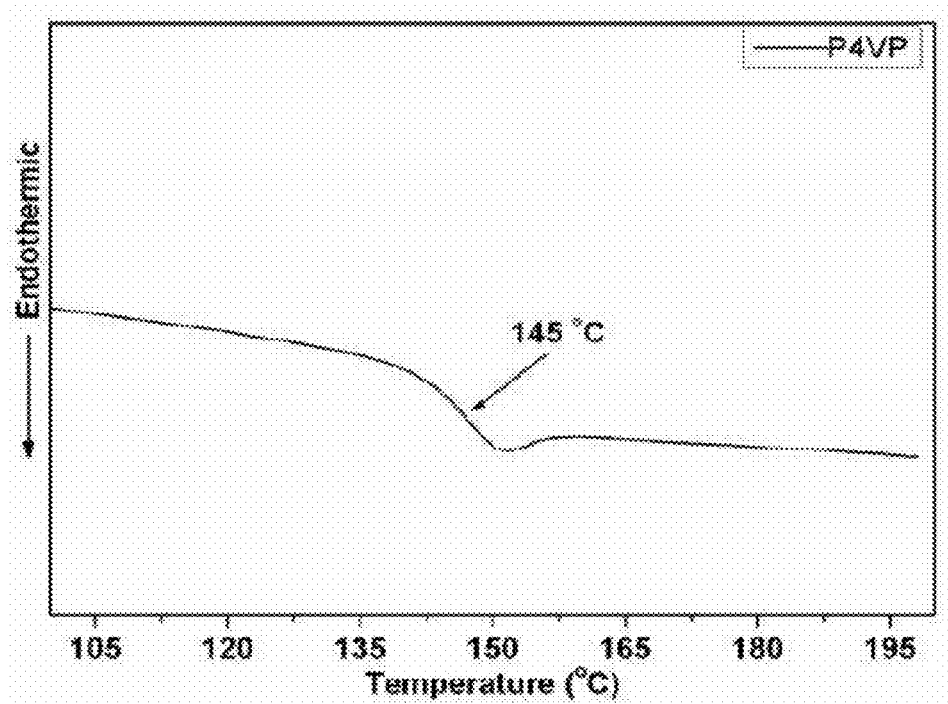
FIG. 5 is a graph representing a differential scanning calorimetry (DSC) thermal curve of the nanoparticles prepared in Example 1.

FIGS. 3(a) to 3(d) are TEM photographs, and FIGS. 3(e) and 3(f) are SEM photographs, of the nanoparticles prepared in Example 1 over time. FIG. 4 is a graph representing a $^1H$ NMR spectrum of nanoparticles prepared in Example 1, and FIG. 5 is a graph representing a thermal curve by a differential scanning calorimetry (DSC) method. Since glass transition temperature was observed at 145° C., it is confirmed that poly 4-vinylpyridine nanoparticles according to Example 1 were prepared. FIG. 2 is a graph with a photograph representing the size of poly 4-vinylpyridine homopolymer nanoparticles over the reaction time of a self-emulsion polymerization.

Example 2 Preparation of Polymethacrylic Acid Homopolymer Nanoparticles

Methacrylic acid (MAA) and 60 mL of water were placed in a 500 mL flask, purged with argon for 30 minutes to remove oxygen, and stirred at 400 rpm at 60° C. for 5 minutes. A hydrophilic initiator (VA-044) was added to the stirred solution, and the solution was stirred under argon atmosphere at 65° C. for 60 minutes, to prepare poly 4-vinylpyridine homopolymer nanoparticles.

The self-emulsion polymerization reaction of polymethacrylic acid (poly-MAA) homopolymer is represented by the following Reaction Formula 2:

[Reaction Formula 2]

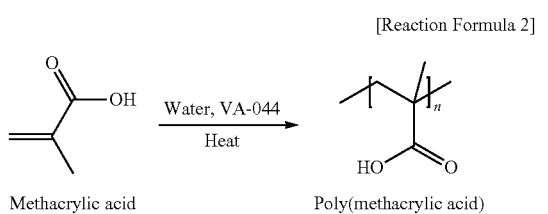

Methacrylic acid → Poly(methacrylic acid)

Figure 6:
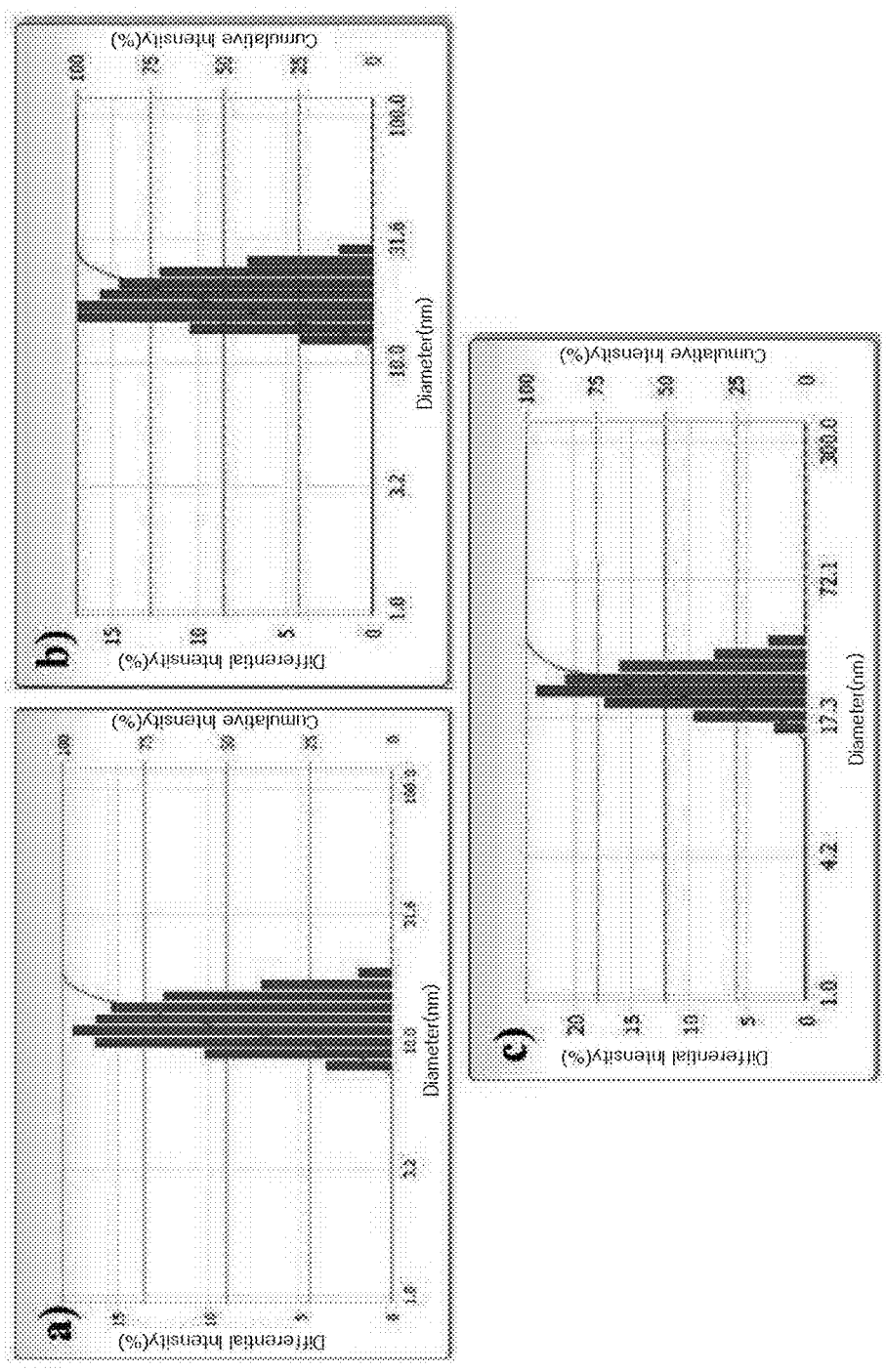
FIGS. 6(a) to 6(c) are graphs representing dynamic light scattering (DLS) measurements of the nanoparticles prepared in Example 2, respectively.

The experiment results depending on the concentrations of methacrylic acid (MAA) and the hydrophilic initiator are summarized in the following Table 4, and DLS measurements are represented in FIG. 6.

TABLE 4

| Monomer MAA (mmol) | Initiator VA-044 (mmol) | Solvent H$_2$O (ml) | Time/Temperature (min/° C.) | Particle size (by DLS in nm) |
|---|---|---|---|---|
| 1.2 | 0.15 | 70 | 120/75 | 66 |
| 1.2 | 0.24 | 70 | 120/75 | 78 |
| 1.2 | 0.08 | 125 | 120/90 | 52 |

Example 3 Preparation of Polyacrylonitrile Homopolymer Nanoparticles

Polyacrylonitrile was prepared in the same manner as in Example 1, using acrylonitrile (AN) instead of 4-vinylpyridine (4-VP). The self-emulsion polymerization reaction of acrylonitrile (AN) homopolymer is represented by following Reaction Formula 3:

[Reaction Formula 3]

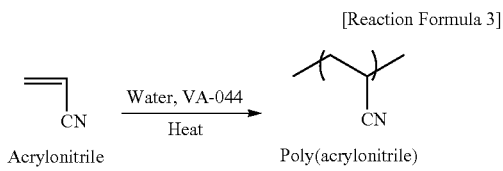

Acrylonitrile → Poly(acrylonitrile)

Figure 7:
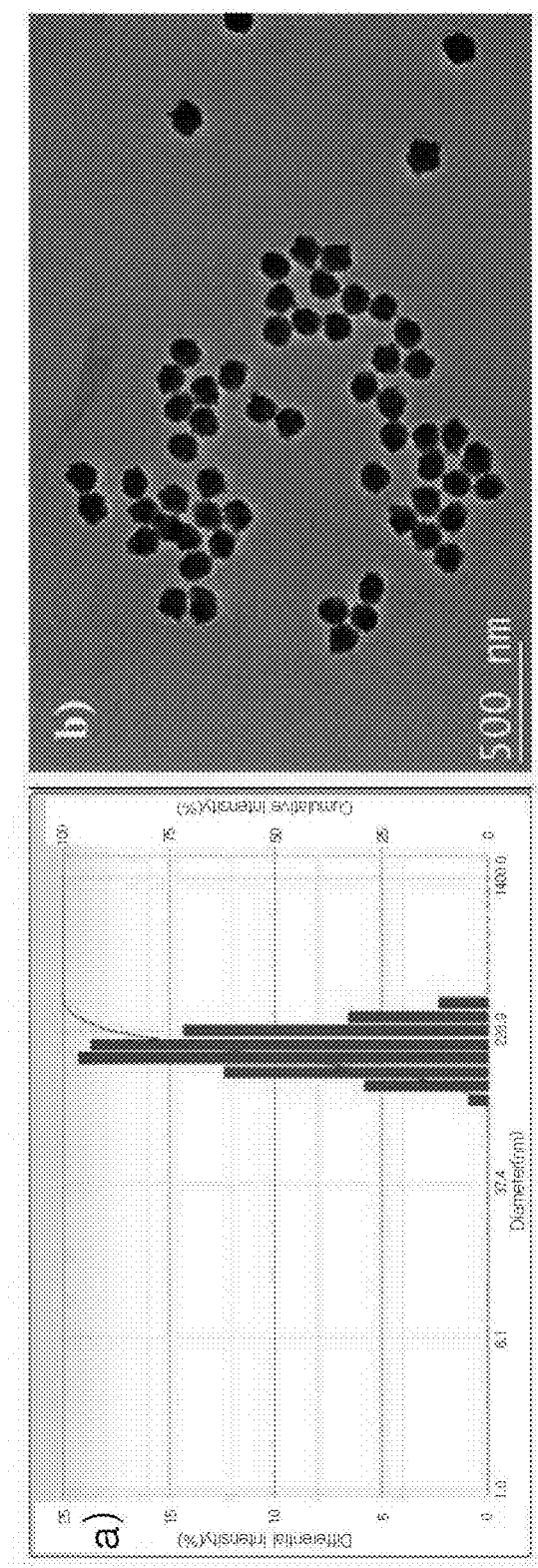
FIG. 7(a) is a DLS photograph.
FIG. 7(b) is a TEM photograph, of the nanoparticles prepared in Example 3, respectively.

FIG. 7(a) is a DLS photograph, and FIG. 7(b) is a TEM photograph, of the nanoparticles prepared in Example 3, respectively.

Example 4 Preparation of poly 4-(4-vinylphenyl)pyridine Homopolymer Nanoparticles Poly 4-(4-vinylphenyl)pyridine was prepared in the same manner as in Example 1, using 4-(4-vinylphenyl)pyridine (P4VPPy) instead of 4-vinylpyridine (4-VP).

The self-emulsion polymerization reaction of 4-(4-vinylphenyl)pyridine (P4VPPy) homopolymer is represented by the following Reaction Formula 4:

[Reaction Formula 4]

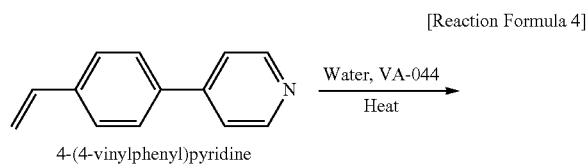

4-(4-vinylphenyl)pyridine

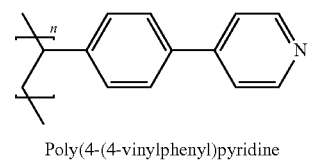

Poly(4-(4-vinylphenyl)pyridine

The experiment results depending on the hydrophilic initiator concentration, the solvent concentration and the temperature are summarized in the following Tables 5:

TABLE 5

| Monomer P4VPPy (mmol) | Initiator VA-044 (mmol) | Solvent (H$_2$O, in ml) | Time/Temperature (min/° C.) | Particle size (by DLS in nm) |
|---|---|---|---|---|
| 1.2 | 0.15 | 70 | 120/75 | 66 |
| 1.2 | 0.24 | 70 | 120/75 | 78 |
| 1.2 | 0.08 | 125 | 120/90 | 52 |

Figure 8:
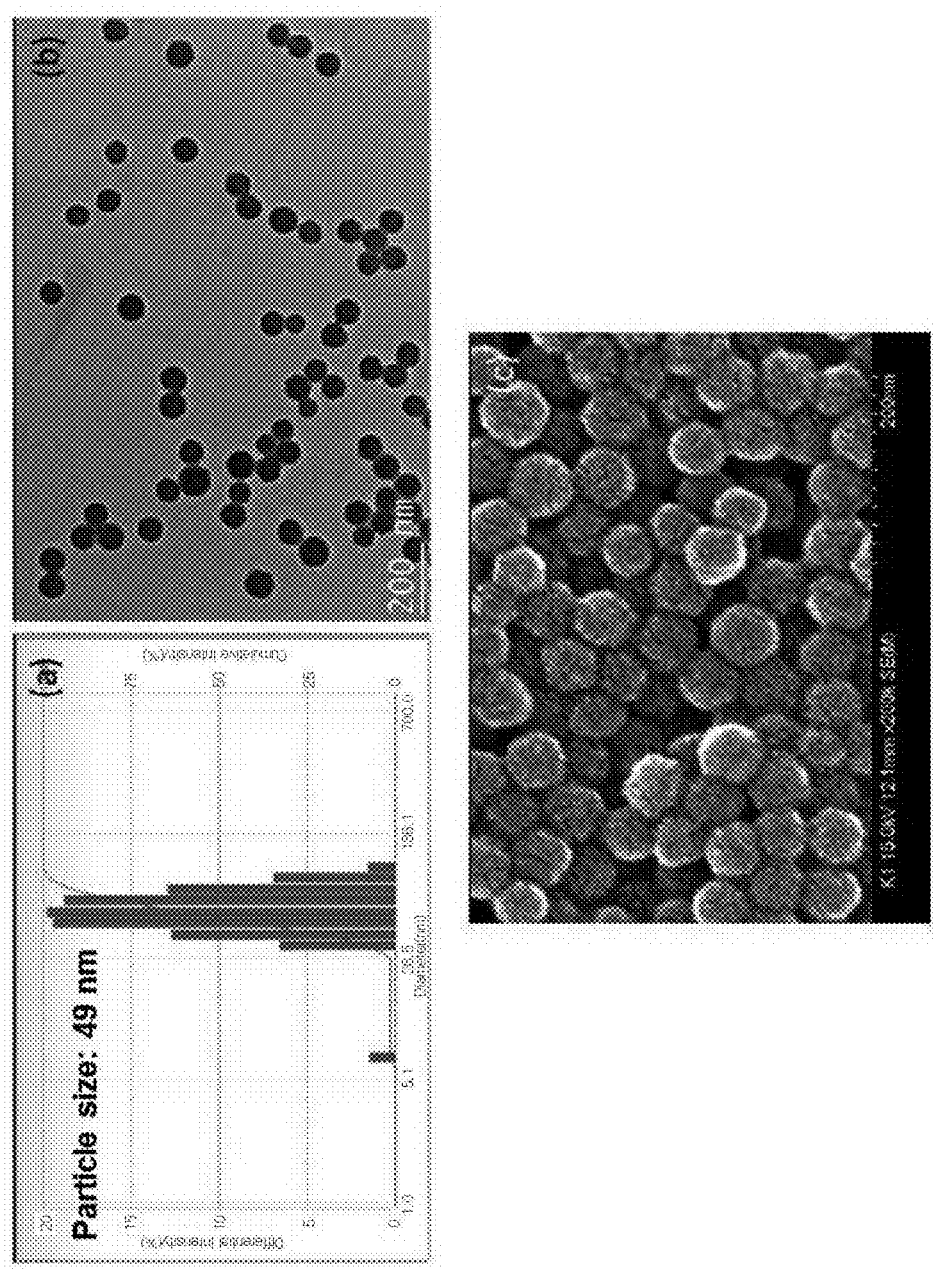
FIG. 8(a) is a graph representing DLS measurements.
FIG. 8(b) is a SEM photograph.
FIG. 8(c) is a TEM photograph, of the nanoparticles prepared in Example 4, respectively.

FIG. 8(a) is a graph representing DLS measurements, and FIG. 8(b) is a SEM photograph, and FIG. 8(c) is a TEM photograph, of the nanoparticles prepared in Example 4, respectively.

Example 5 Preparation of Poly N-Vinylpyrrolidone Homopolymer Nanoparticles

Poly N-vinylpyrrolidone was prepared in the same manner as in Example 1, using N-vinylpyrrolidine (N-VP) instead of 4-vinylpyridine (4-VP).

The self-emulsion polymerization reaction of N-vinylpyrrolidine (N-VP) homopolymer is represented by the following Reaction Formula 5:

[Reaction Formula 5]

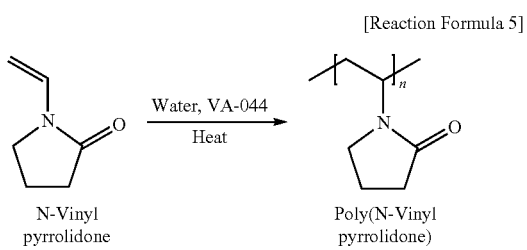

N-Vinyl pyrrolidone → Poly(N-Vinyl pyrrolidone)

Figure 9:
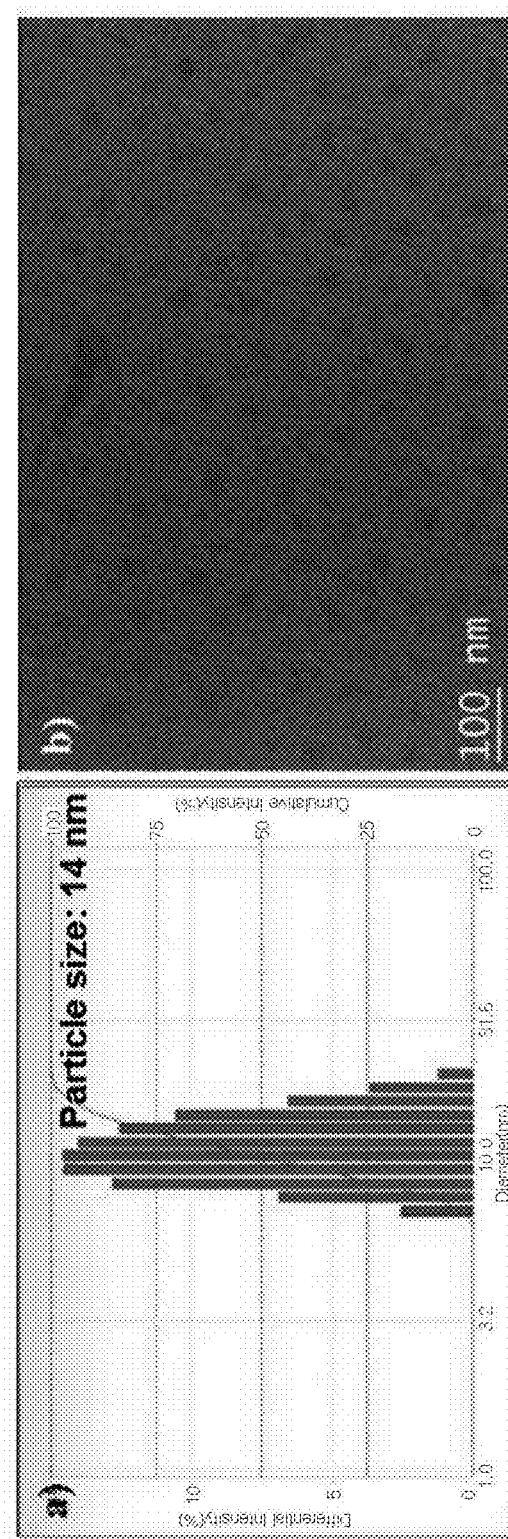
FIG. 9(a) is a graph representing DLS measurements.
FIG. 9(b) is a TEM photograph, of the nanoparticles prepared in Example 5, respectively.

FIG. 9(a) is a graph representing DLS measurements, and FIG. 9(b) is a TEM photograph, of the nanoparticles prepared in Example 5, respectively.

Example 6 Preparation of Poly 2-Hydroxyethyl Methacrylate Homopolymer Nanoparticles Poly 2-hydroxyethyl methacrylate was prepared in the same manner as in Example 1, using 2-hydroxyethyl methacrylate (HEMA) instead of 4-vinylpyridine (4-VP).

The self-emulsion polymerization reaction of 2-hydroxyethyl methacrylate (HEMA) homopolymer is represented by the following Reaction Formula 6:

[Reaction Formula 6]

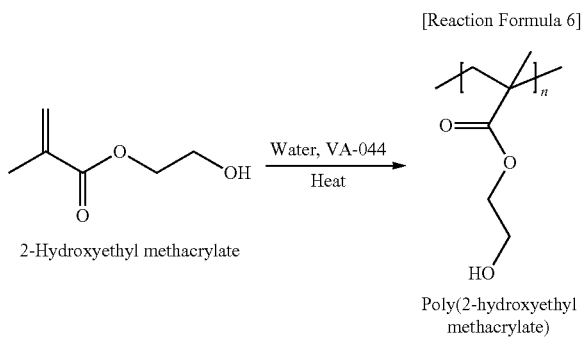

2-Hydroxyethyl methacrylate

Poly(2-hydroxyethyl methacrylate)

Figure 10:
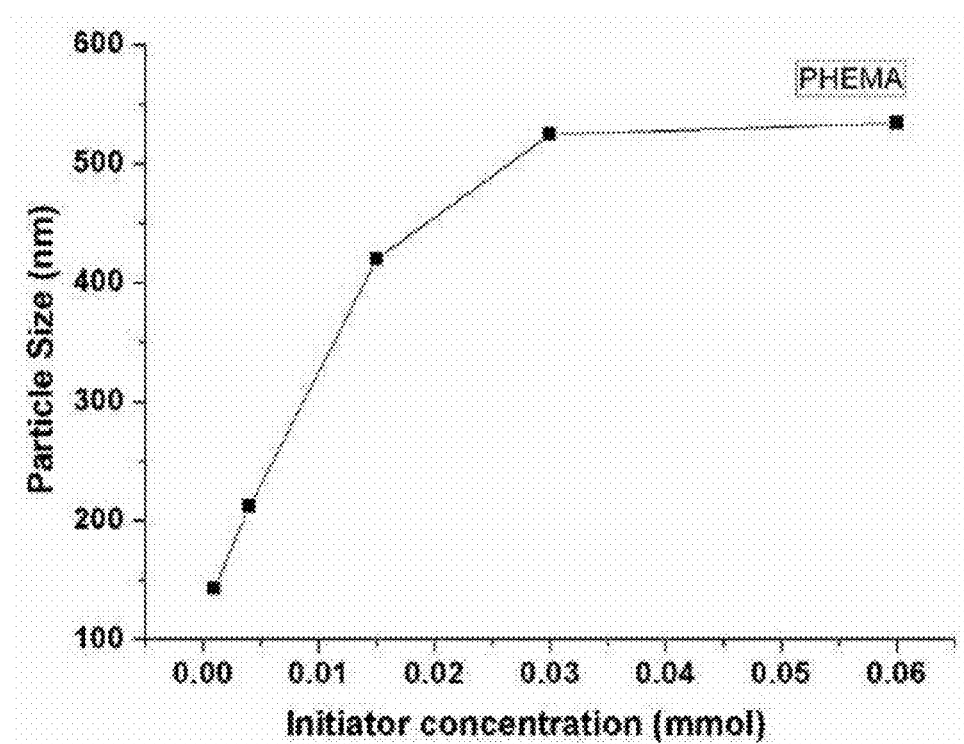
FIG. 10 is a graph representing the size of the nanoparticles prepared in Example 6 depending on the concentration of a hydrophilic initiator.
Figure 11:
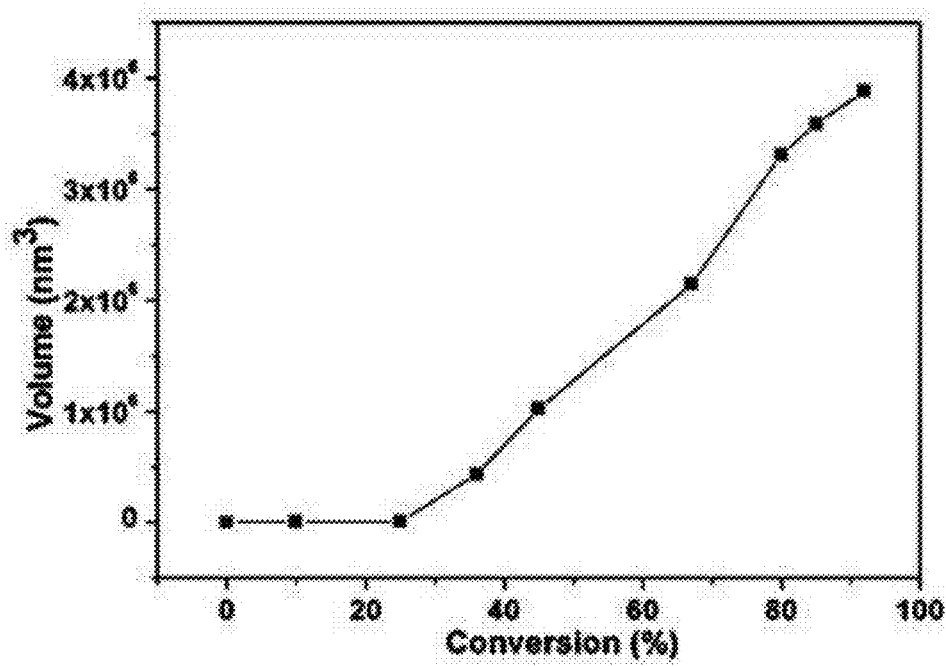
FIG. 11 is a graph representing the conversion rate measured on the homopolymer nanoparticles according to an exemplary embodiment.

The experiment results depending on the concentration of the hydrophilic initiator are summarized in the following Table 6, and represented by a graph in FIG. 10.

TABLE 6

| Monomer HEMA (mmol) | Initiator VA-044 (mmol) | Solvent H$_2$O (ml) | Time/Temperature (min/° C.) | Particle size (by DLS in nm) |
|---|---|---|---|---|
| 1.53 | 0.001 | 60 | 120/65 | 143 |
| 1.53 | 0.004 | 60 | 120/65 | 212 |
| 1.53 | 0.015 | 60 | 120/65 | 420 |
| 1.53 | 0.030 | 60 | 120/65 | 525 |
| 1.53 | 0.060 | 60 | 120/65 | 534 |

Example 7 Preparation of Polymethylmethacrylate Homopolymer Nanoparticles

Figure 12:
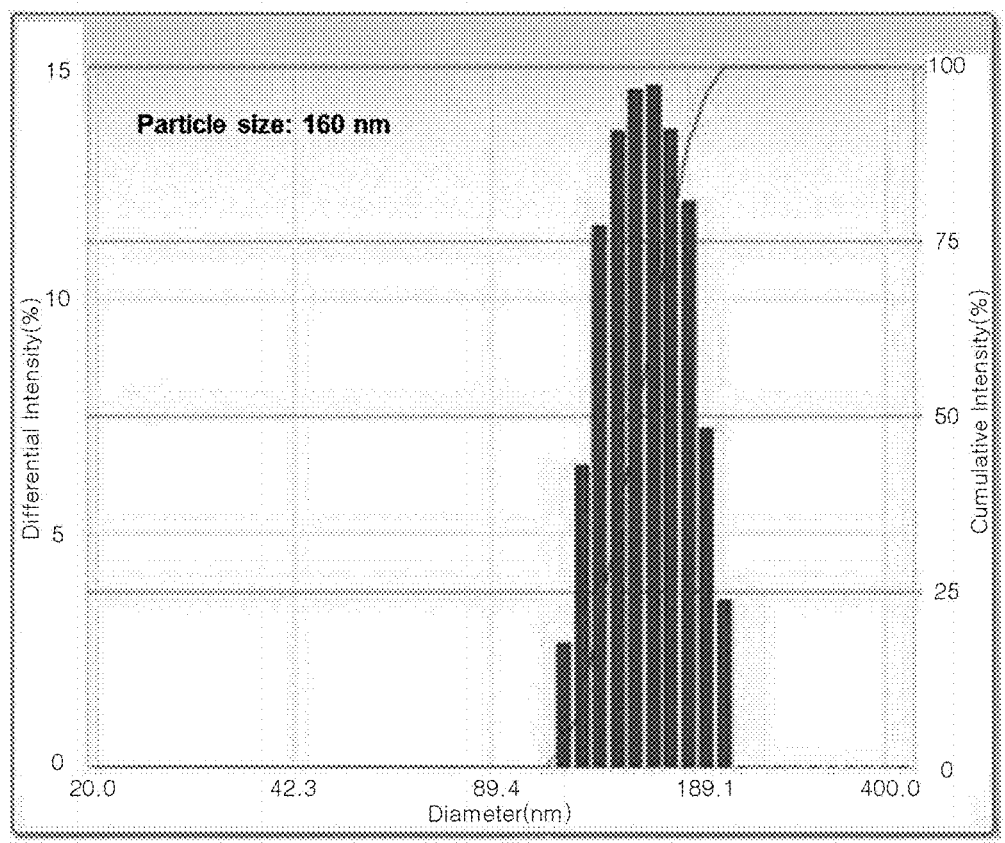
FIG. 12 is a graph representing DLS measurements of the nanoparticles prepared in Example 7.

Polymethylmethacrylate was prepared in the same manner as in Example 1, using methylmethacrylate instead of 4-vinylpyridine (4-VP). FIG. 12 is a graph representing dynamic light scattering (DLS) measurements of the nanoparticles prepared in Example 7, respectively.

The self-emulsion polymerization reaction of methylmethacrylate homopolymer is represented by the following Reaction Formula 7:

[Reaction Formula 7]

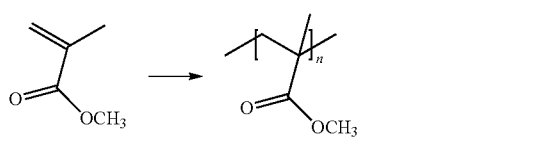

The reaction material, the reaction condition, and the size of the produced homopolymer nanoparticles are summarized in the following Table 7:

TABLE 7

| Monomer MMA (mmol) | Initiator VA-044 (mmol) | Solvent (H$_2$O, in ml) | Time/Temperature (min/° C.) | Particle size (by DLS in nm) |
|---|---|---|---|---|
| 4.9 | 0.049 | 60 | 120/65 | 160 |

Figure 13:
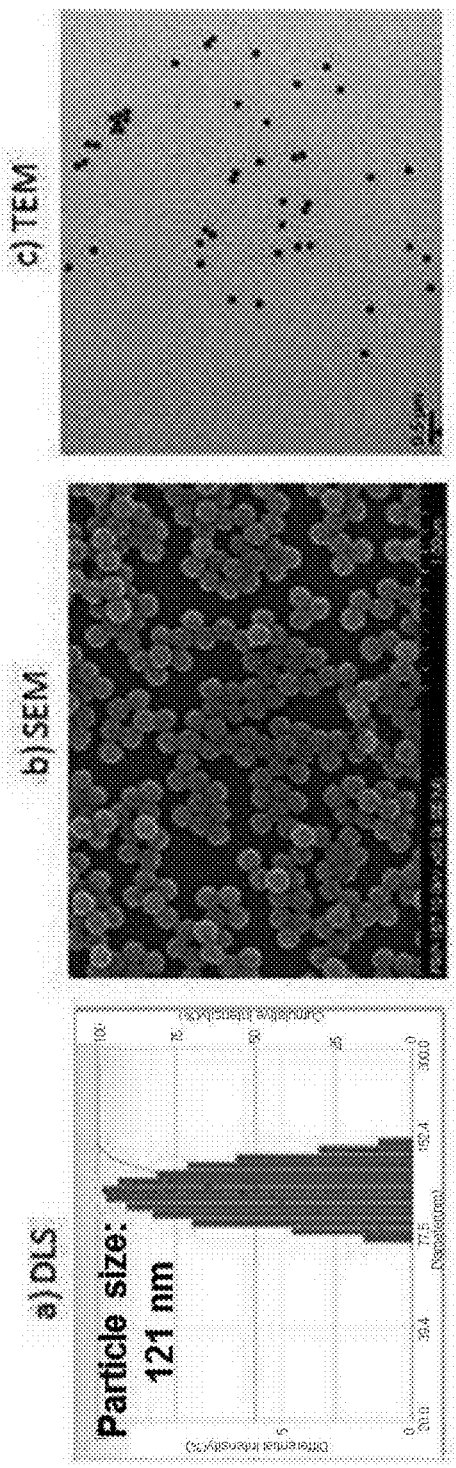
FIG. 13(a) is a graph representing DLS measurements.
FIGS. 13(b) and 13(c) are SEM and TEM photographs, of the nanoparticles prepared in Example 8, respectively.

Example 8 Preparation of poly 6-vinylpyridin-3-carbonitrile Homopolymer Nanoparticles Poly 6-vinylpyridin-3-carbonitrile was prepared in the same manner as in Example 1, using 6-vinylpyridin-3-carbonitrile (VPyCN) instead of 4-vinylpyridine (4-VP). FIG. 13(*a*) is a graph representing DLS measurements, and FIGS. 13(*b*) and 13(*c*) are SEM and TEM photographs, of the homopolymer nanoparticles prepared in Example 8, respectively.

The self-emulsion polymerization reaction of 6-vinylpyridin-3-carbonitrile (VPyCN) homopolymer is represented by the following Reaction Formula 8:

[Reaction Formula 8]

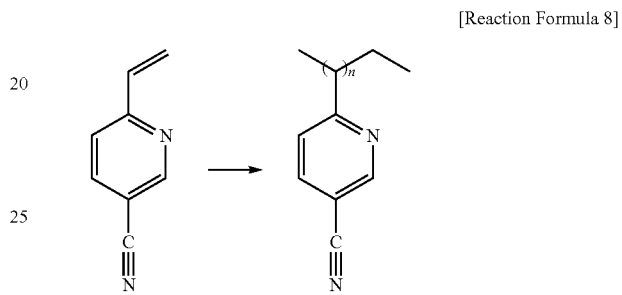

The reaction material, the reaction condition, and the size of produced homopolymer nanoparticles are summarized in the following Table 8:

TABLE 8

| Monomer VPyCN (mmol) | Initiator VA-044 (mmol) | Solvent (H$_2$O, in ml) | Time/Temperature (min/° C.) | Particle size (by DLS in nm) |
|---|---|---|---|---|
| 1.53 | 0.076 | 30 | 120/65 | 121 |

Relationship with Initiator Concentration

As seen from Tables 1, 4 and 5, the size of the nanoparticles has a nearly linear function relationship with the concentration of the initiator. As the concentration of the initiator decreases, the chain of long homopolymer has low concentration. This means that small polymerization nucleus is formed, which causes nanoparticles to have small size.

Relationship with Solvent

If the volume of water which is a solvent is increased, the amount of monomers dissolved in water is increased. Thus, small-sized particles are made, and the sites of homogeneous nucleus are increased, which may be confirmed in Table 2.

Relationship with Temperature

The effect of temperature on a nanoparticle size was studied. As temperature increases, the size of homopolymer nanoparticles of the present invention tends to decrease. This may be because the decomposition of the initiator occurs at high temperature, and thus, the number of monomers per a growth chain is decreased. As a result, more ionic groups form smaller-sized particles, and affect stabilization.

Evaluation Example 1. Shape Factor Measurement

In order to more observe a growth mechanism, shape factor ρ ($R_g/R_h$; $R_g$ is a turning radius, and $R_h$ is a hydrodynamic radius) which is useful to analyze a nanoparticle structure like a micelle, was measured. If $R_g/R_h$ is close to 1, a hollow structure is formed; and if $R_g/R_h$ is close to 0.7, a solid sphere is formed. When the polymerization reaction time of poly 4-vinylpyridine homopolymer nanoparticles is 2, 20 and 60 minutes, shape factor ρ was 0.97, 0.76 and 0.73, respectively.

Evaluation Example 2. Conversion Rate of Monomer and SEP Analysis

In order to calculate conversion rate (%) of monomer, further polymerization reaction was carried out, and the monomer conversion rate was calculated by gravimetry. The samples of poly 4-vinylpyridine homopolymer nanoparticles at various reaction polymerization times were transferred from a reaction flask to an aluminum cup, dried, and weighed. The solvent in the cup was evaporated at room temperature, and the remaining product was dried at 80° C. until it has a constant weight.

The synthesis rate of homopolymer nanoparticles from the samples at 60 minutes of reaction time was 92%, and most of the monomers were polymerized to nanoparticles having a size of 200±5 nm.

Using the sample at 60 minutes of reaction time, size exclusion chromatography (SEC) was carried out. High number average molecular weight $M_n$ was 209418 g/mol, and unimodal but broad molecular weight $M_w/M_n$ was 1.52. These values show that the SEP method also behaves like a free radical polymerization reaction carried out in a water-based medium.

The present invention provides a preparation method of homopolymer nanoparticles by a self-emulsion polymerization reaction using only water, an amphiphilic monomer and a hydrophilic initiator, and homopolymer nanoparticles prepared thereby, wherein the amphiphilic monomer or homopolymer itself serves as a surfactant to form a micelle. Since the method uses no surfactant, its preparation process is simple and environment-friendly, so as to safely prepare nanoparticles, and thus prepared homopolymer nanoparticles may be used in various fields such as a drug delivery material, an electron transport layer, and the like.

What is claimed is:

1. A preparation method of homopolymer nanoparticles comprising:
   (i) preparing a deoxygenated mixture of water and an amphiphilic monomer selected from the group consisting of vinylpyridine, 4-vinylpyridine, acrylic acid, methacrylic acid, styrene sulfonic acid, 4-styrene sulfonic acid, 2-hydroxyethyl methacrylate, hydroxypropyl methacrylate, hydroxybutyl methacrylate, methacrylamide, n-vinylpyrrolidone, acrylonitrile, 4-(4-vinylphenyl)pyridine, and 6-vinylpyridine-3-carbonitrile;
   (ii) adding a hydrophilic initiator to said mixture to initiate a surfactant-free polymerization reaction of amphiphilic monomers;
   (iii) carrying out the surfactant-free polymerization reaction at constant temperature ranging from 55° C. to 95° C. for 50-160 minutes to form the homopolymer nanoparticles.

2. The preparation method of homopolymer nanoparticles of claim 1, wherein the homopolymer is represented by one of the following Chemical Formulae 1-7:

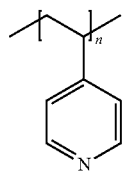
[Chemical Formula 1]

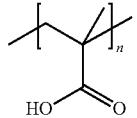
[Chemical Formula 2]

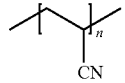
[Chemical Formula 3]

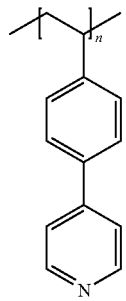
[Chemical Formula 4]

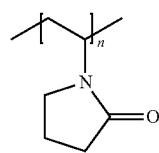
[Chemical Formula 5]

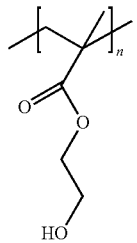
[Chemical Formula 6]

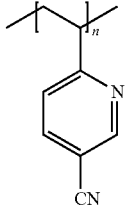
[Chemical Formula 7]

wherein n is an integer of 10 to 10,000.

3. The preparation method of homopolymer nanoparticles of claim 1, wherein the hydrophilic initiator is at least one selected from the group consisting of 2,2'-azobis[2-(2-imidazolin-2-yl)propane]dihydrochloride, 4,4-azobis(4-cyanovaleric acid), ammonium persulfate, potassium persulfate, sodium persulfate, ammonium bisulfate, sodium bisulfate and 1,1-azobis(1-methylbutyronitrile-3-sodium sulfonate).

4. Homopolymer nanoparticles comprising a homopolymer represented by one of the following Chemical Formulae 1-7:

[Chemical Formula 1]

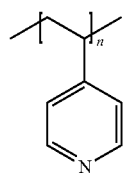

[Chemical Formula 2]

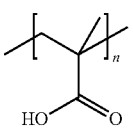

[Chemical Formula 3]

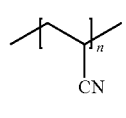

[Chemical Formula 4]

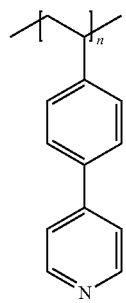

[Chemical Formula 5]

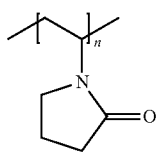

[Chemical Formula 6]

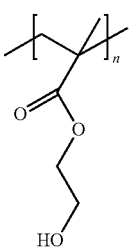

[Chemical Formula 7]

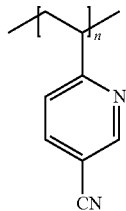

wherein n is an integer of 10 to 10,000; and wherein said nanoparticles consist of 2-1,000 homopolymers; have a spherical shape having a diameter of 1-800 nm; and have a shell composed of hydrophilic pendants of said homopolymers and an inner layer composed of 70-95 vol % of hydrophobic main chains of said homopolymers and 5-30 vol % of hydrophilic pendants of said homopolymers.

5. The homopolymer nanoparticles of claim 4 prepared by the preparation method of claim 1.

6. A drug delivery material comprising the homopolymer nanoparticles of claim 4 and a pharmaceutical active material collected in the inner layer of the homopolymer nanoparticles.

7. A preparation method of homopolymer nanoparticles comprising:
(i) preparing a deoxygenated mixture of water and an amphiphilic monomer selected from the group consisting of vinylpyridine, 4-vinylpyridine, acrylic acid, methacrylic acid, styrene sulfonic acid, 4-styrene sulfonic acid, 2-hydroxyethyl methacrylate, hydroxypropyl methacrylate, hydroxybutyl methacrylate, methacrylamide, n-vinylpyrrolidone, acrylonitrile, 4-(4-vinylphenyl)pyridine, and 6-vinylpyridine-3-carbonitrile;
(ii) adding a hydrophilic initiator to said mixture to initiate a surfactant-free polymerization reaction of amphiphilic monomers;
(iii) carrying out a surfactant-free polymerization reaction at constant temperature ranging from 55° C. to 95° C. for 50-160 minutes to form the homopolymer nanoparticles;
(iv) swelling the homopolymer nanoparticles and collecting a pharmaceutical active material in an inner layer of said nanoparticles.

8. The preparation method of homopolymer nanoparticles of claim 7, wherein the hydrophilic initiator is at least one selected from the group consisting of 2,2'-azobis[2-(2-imidazolin-2-yl)propane]dihydrochloride, 4,4-azobis(4-cyanovaleric acid), ammonium persulfate, potassium persulfate, sodium persulfate, ammonium bisulfate, sodium bisulfate and 1,1-azobis(1-methylbutyronitrile-3-sodium sulfonate).

* * * * *